United States Patent [19]

Tachizawa et al.

[11] Patent Number: 5,696,070
[45] Date of Patent: Dec. 9, 1997

[54] QUARTERNARY AMMONIUM SALT, METHOD FOR PRODUCTION THEREOF, AND SOFTENER COMPOSITION USING SALT

[75] Inventors: Osamu Tachizawa; Akira Sakaguchi; Tohru Katoh, all of Wakayama; Kohshiro Sotoya, deceased, late of Wakayama, by Youko Sotoya, Hidetsugu Sotoya, Shigehiko Sotoya, heirs; Noriko Yamaguchi, Wakayama; Junichi Inokoshi, Wakayama; Muneo Aoyagi, Wakayama, all of Japan

[73] Assignee: Kao Corporation, Tokyo, Japan

[21] Appl. No.: 605,916

[22] Filed: Feb. 23, 1996

[30] Foreign Application Priority Data

Feb. 24, 1995 [JP] Japan ................................ 7-036727
Mar. 2, 1995 [JP] Japan ................................ 7-042806

[51] Int. Cl.$^6$ ................. A61K 7/08; C07C 211/62; C11D 1/62; D06M 13/46
[52] U.S. Cl. ................. 510/123; 424/70.28; 510/515; 510/527; 554/109; 554/114
[58] Field of Search ................. 510/515, 527, 510/123, 124; 554/109, 114; 424/70.28

[56] References Cited

FOREIGN PATENT DOCUMENTS

| | | |
|---|---|---|
| 309 052 | 3/1989 | European Pat. Off. . |
| 409 504 | 1/1991 | European Pat. Off. . |
| A-01-162872 | 6/1989 | Japan . |
| A-03-90677 | 4/1991 | Japan . |
| 91/16880 | 11/1991 | WIPO . |

OTHER PUBLICATIONS

Chemical Abstracts, vol. 114, No. 20, 20 May 1991, Columbus Ohio, US; abstract No. 198049, Shoichiro Yasunami: "Solid polyoxyalkylene-derived electrolyte with coatability," XP002003717 * abstract * & JP-A-02 274 728.

Chemical Abstracts, vol. 114, No. 14, 8 Apr. 1991, Columbus Ohio, US; abstract No. 124167, Shigetoshi ONO: "Electric conductive polymer laminates", XP002003718 * abstract * & JP-A-02 249 643.

*Primary Examiner*—Anthony Green
*Attorney, Agent, or Firm*—Oblon, Spivak, McClelland, Maier & Neustadt, P.C.

[57] ABSTRACT

A liquid softener composition comprising a quaternary ammonium salt represented by the general formula (1) and a method for its preparation:

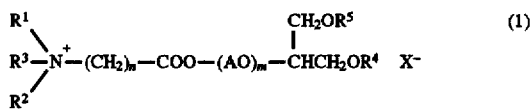

$$R^3-\overset{R^1}{\underset{R^2}{\overset{|}{N^+}}}-(CH_2)_n-COO-(AO)_m-\overset{CH_2OR^5}{\underset{}{\overset{|}{C}}}HCH_2OR^4 \quad X^- \quad (1)$$

wherein $R^1$, $R^2$, and $R^3$ are an alkyl group or hydroxyalkyl group of 1 to 4 carbon atoms, $R^4$ and $R^5$ are an unsubstituted or hydroxyl group-substituted linear or branched alkyl group or alkenyl group of 8 to 36 carbon atoms, A is a linear or branched alkylene group of 2 or 3 carbon atoms, X is an anion group, n is an integer in the range of 1 to 6, and m is a numeral in the range of 0 to 20.

12 Claims, No Drawings

QUARTERNARY AMMONIUM SALT, METHOD FOR PRODUCTION THEREOF, AND SOFTENER COMPOSITION USING SALT

FIELD OF THE INVENTION

This invention relates to a novel quaternary ammonium salt and a method for the production thereof. More particularly, this invention relates to a quaternary ammonium salt which imparts notable softness to fibers, confers notable softness and smoothness on hair, and moreover excels in biodegradability and a method for the production thereof.

DESCRIPTION OF RELATED ART

The material now marketed as softener compositions for fibers or hair treating agents are virtually wholly made of compositions containing quaternary ammonium salts having two long-chain alkyl groups in the molecular unit thereof as represented by di(hardened tallow alkyl) dimethyl ammonium chloride.

The quaternary ammonium salts mentioned above, however, create a problem in that their residues after intended use, when released into the natural environment including such bodies of water as rivers and brooks, nearly wholly escape biodegradation and accumulate therein. To obviate this problem, improved compositions as incorporating methylbis[hardened beef tallow alkanoyloxyethyl]-2-hydroxyethyl ammonium methyl sulfate, dimethylbis[alkanoyloxyethyl]-ammonium chloride, etc. therein have been introduced to the market. These compounds indeed have improved biodegradability as compared with the quaternary ammonium salts mentioned above. They, however, can hardly be regarded as bases satisfactory in terms of softness and environmental safety.

JP-A-01-162,872 discloses a biodegradable quaternary ammonium salt containing a linear alkoxylated alcohol and JP-A-03-90,677 discloses a composition for softening fibrous products.

DESCRIPTION OF THE INVENTION

It is, therefore, an object of this invention to provide a quaternary ammonium salt suitable as a softening material which excels in softness and having proper biodegradability.

The present inventors have found a novel quaternary ammonium salt which best fits the object mentioned above.

To be specific, this invention aims to provide a novel quaternary ammonium salt represented by the general formula (1) and a method for the production of this salt.

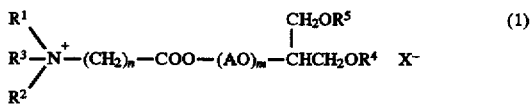
(1)

(wherein $R^1$, $R^2$, and $R^3$ are the same or different from each other and are alkyl groups or hydroxyalkyl groups containing 1 to 4 carbon atoms, $R^4$ and $R^5$ are the same or different from each other and are unsubstituted or hydroxyl group-substituted linear or branched alkyl groups or alkenyl groups containing 8 to 36 carbon atoms, A is a linear or branched alkylene group of 2 or 3 carbon atoms, X is an anion group, n is an integer in the range of 1 to 6, and m is a numeral in the range of 0 to 20 indicating the average number of addition mols of an alkylene oxide).

This quaternary ammonium salt is useful for softly finishing fibers and fibrous products.

It is also useful for beautifying hair.

Preferably, in the general formula (1), $R^1$, $R^2$, and $R^3$ each is a methyl group, an ethyl group, or a hydroxy-ethyl group, $R^4$ and $R^5$ each is a linear alkyl group of 12 to 22 carbon atoms, A is for

X is a halogen atom, a sulfate, an optionally hydroxyl group-substituted carboxylate of 1 to 4 carbon atoms or an alkyl sulfate of 1 to 4 carbon atoms, n is an integer in the range of 1 to 3, and m is a numeral in the range of 0 to 10.

This invention further provides a method for the production of the quaternary ammonium salt mentioned above, characterized by reacting a glycerol compound represented by the general formula (2)

(2)

(wherein $R^4$, $R^5$, A, and m have the same meanings as defined above) with a compound represented by the general formula (3)

(3)

(wherein $R^6$ is a hydrogen atom or an alkyl group of 1 to 4 carbon atoms and Y is a halogen atom, and n esterifying the compound of the formula (3) and obtaining a haloester effecting esterification and obtaining a haloester represented by the general formula (4)

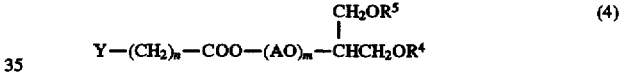
(4)

(wherein $R^4$, $R^5$, A, Y, n and m have the same meanings as defined above), and further reacting this haloester with a tertiary amine represented by the general formula (5)

(5)

(wherein $R^1$, $R^2$, and $R^3$ have the same meanings as defined above).

Further, this invention provides a method for the production of the quaternary ammonium salt mentioned above, characterized by reacting a haloester represented by the general formula (4) mentioned above to react with a secondary amine represented by the general formula (6)

(6)

(wherein $R^1$ and $R^2$ have the same meanings as defined above) thereby forming an aminoester represented by the general formula (7)

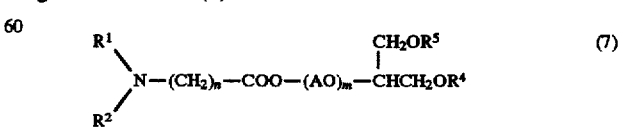
(7)

(wherein $R^1$, $R^2$, $R^4$, $R^5$, A, n, and m have the same meanings as defined above), and further causing a quaternizing agent represented by the general formula (8)

R³X  (8)

with the amino ester of the general formula (7) (wherein R³ and X have the same meanings as defined above).

This invention provides a liquid softener composition or a composition for a hair treating agent, comprising (A) the quaternary ammonium salt mentioned above and water the amount of the (A) component being in the range of 2 to 40% by weight based on the amount of the composition.

In the composition, the (A) component is represented by the general formula (I-1).

$$\begin{array}{c} CH_3 \\ | \\ -CH_2CH_2- \text{ or } -CHCH_2-, \end{array}$$  (I-1)

(wherein $R^1$, $R^2$, $R^3$, n, and $X^-$ have the same meanings as defined above).

Preferably, in the composition, $R^1$, $R^2$ and $R^3$ are a methyl group and $R^4$ and $R^5$ are a linear or branched alkyl group of 12 to 24 carbon atoms.

The composition can further incorporate therein the following components (B), (C), (D), (E), and (F) respectively up to the upper limits of 20 wt. %, 20 wt. %, 10 wt. %, 10 wt. %, and 10 wt. %.

(B): A linear or branched saturated or unsaturated alcohol of 8 to 44 carbon atoms.

(C): A linear or branched saturated or unsaturated fatty acid of 8 to 36 carbon atoms.

(D): A monohydric alcohol of one to four carbon atoms.

(E): A polyether compound obtained by alkoxylation with ethylene oxide and optionally propylene oxide and/or trimethylene oxide of a compound having three or more active hydrogen atoms, the polyether compound having a weight average molecular weight in the range of 5,000 to 2,000,000, and having oxyethylene groups in an amount of not less than 55% by weight based on the molecular weight of the polyether compound.

(F): A nonionic surfactant of a linear or branched saturated or unsaturated alcohol of 8 to 24 carbon atoms alkoxylated with 5 to 50 mols of ethylene oxide, propylene oxide or mixture thereof.

The present invention further pertains to a method for soft-finishing fibers by the treatment thereof with the composition defined above and to use of the composition in the treatment of a product of fibers for the purpose of softening the product.

Now, this invention will be described in detail below.

In the general formula (1) which represents the quaternary ammonium salt of this invention, $R^1$, $R^2$, and $R^3$ are the same or different from each other are an alkyl group or hydroxyalkyl group containing 1 to 4 carbon atoms. As concrete examples of the alkyl group or hydroxyalkyl group, methyl, ethyl, propyl, butyl, hydroxyethyl, and other groups may be cited. Among them, methyl, ethyl, and hydroxyethyl group are preferred methyl groups being most preferred.

Then, $R^4$ and $R^5$ are the same or different from each and are unsubstituted or hydroxyl group-substituted linear or branched alkyl group or alkenyl group containing 8 to 36 carbon atoms. As specific examples of the group mentioned above, decyl, dodecyl, tetradecyl, hexadecyl, octadecyl, hydroxyoctadecyl, docosyl, and other groups may be cited. Among them, linear alkyl groups of 12 to 22 carbon atoms are preferable, octadecyl and hexadecyl group and the mixture thereof are more preferable, and octadecyl group is most preferable. Advantageously $R^4$ and $R^5$ stand for the same group.

A is a linear or branched alkylene group of two or three carbon atoms. A preferably is $$\begin{array}{c} CH_3 \\ | \\ -CH_2CH_2- \text{ or } -CHCH_2-, \end{array}$$

and more preferably an ethylene group. m is a numeral of 0 to 20, preferably 0 to 10, and more preferably 0, indicating the average number of addition mols of alkylene oxide. n is an integer of 1 to 6, preferably 1 to 3, and more preferably 1. X is an anion group, preferably a halogen atom, sulfate, an unsubstituted or hydroxyl group-substituted carboxylate of 1 to 4 carbon atoms or an alkyl sulfate of 1 to 4 carbon atoms, and more preferably Cl or $CH_3SO_4$.

As specific examples of the quaternary ammonium salt which is represented by the general formula (1), the following compounds may be cited.

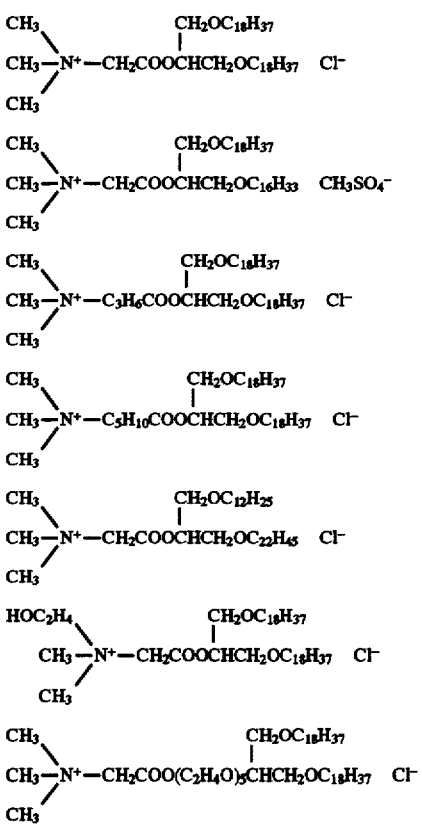

The quaternary ammonium salt of this invention represented by the general formula (1) mentioned above (hereinafter referred to briefly as "quaternary ammonium salt (1)") can be produced by the following methods 1 and 2 of production.

<Method of 1 of production>

This method obtain the quaternary ammonium salt (1) by reacting a glycerol compound represented by the general formula (2)

$$\begin{array}{c} CH_2OR^5 \\ | \\ HO-(AO)_m-CHCH_2OR^4 \end{array}$$  (2)

(wherein $R^4$, $R^5$, A, and m have the same meanings as defined above) with a compound represented by the general formula (3)

$$Y-(CH_2)_n-COOR^6$$  (3)

(wherein $R^6$ stands for a hydrogen atom or an alkyl group of 1 to 4 carbon atoms and Y for a halogen atom, and n has the same meaning as defined above) thereby to esterify the compound of formula (3) and producing a haloester represented by the general formula (4)

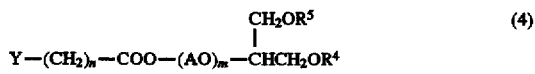

$$Y-(CH_2)_n-COO-(AO)_m-\overset{\overset{\displaystyle CH_2OR^5}{|}}{CHCH_2OR^4} \quad (4)$$

(wherein $R^4$, $R^5$, A, Y, n and m have the same meanings as defined above), and further reacting this haloester with a tertiary amine represented by the general formula (5)

$$\begin{matrix} R^1 \\ \phantom{R^3}\diagdown \\ R^3-N \\ \phantom{R^2}\diagup \\ R^2 \end{matrix} \quad (5)$$

optionally subjecting the quaternized aminoester to salt exchange. (wherein $R^1$, $R^2$, and $R^3$ have the same meanings as defined above).

<Method 2 of production>

This method obtains the quaternary ammonium salt (1) by reacting a haloester represented by the general formula (4) mentioned above with a secondary amine represented by the general formula (6)

$$\begin{matrix} R^1 \\ \phantom{.}\diagdown \\ \phantom{..}N-H \\ \phantom{.}\diagup \\ R^2 \end{matrix} \quad (6)$$

(wherein $R^1$ and $R^2$ have the same meanings as defined above) thereby forming an aminoester represented by the general formula (7)

$$\begin{matrix} R^1 \\ \phantom{.}\diagdown \\ \phantom{..}N-(CH_2)_n-COO-(AO)_m-\overset{\overset{\displaystyle CH_2OR^5}{|}}{CHCH_2OR^4} \\ \phantom{.}\diagup \\ R^2 \end{matrix} \quad (7)$$

(wherein $R^1$, $R^2$, $R^4$, $R^5$, A, n, and m have the same meanings as defined above), and further reacting a quaternizing agent represented by the general formula (8) to react with the aminoester of the formula (7)

$$R^3X \quad (8)$$

(wherein $R^3$ and X have the same meanings as defined above) and optionally subjecting the quaternized aminoester to salt exchange.

Now, the methods for producing the quaternary ammonium salt (1) will be described in detail below.

In the method 1 of production, first the haloester represented by the general formula (4) is obtained by esterifying the compound represented by the general formula (3) used in an amount in the range of 0.9 to 2.0 times mol, preferably 1.0 to 1.5 times mol, per mol of the glycerol represented by the general formula (2) at a temperature in the range of 70° to 200° C., preferably 100° to 150° C., optionally in the presence of a catalyst for a period in the range of 1 to 20 hours.

As specific examples of the glycerol, represented by the general formula (2) used herein, 1,3-dioctadecanoxy-2-propanol, 1-octadecanoxy-3-hexadecanoxy-2-propanol, 1-dodecanoxy-3-docosanoxy-2-propanol, ethylene oxide adducts and propylene oxide adducts thereof, and mixtures thereof may be cited.

As specific examples of the compound represented by the general formula (3), monochloroacetic acid, monochlorobutyric acid, monochlorohexanoic acid, and methyl esters and ethyl esters thereof may be cited. The catalysts which are usable for the esterification include such acid catalysts as p-toluenesulfonic acid and sulfuric acid, for example.

Then, the quaternary ammonium salt (1) can be obtained by quaternizing the haloester represented by the general formula (4) obtained as described above and the tertiary amine represented by the general formula (5) used in an amount in the range of 0.9 to 5.0 times mol, preferably 0.95 to 2.0 times mol, per mol of the haloester at a temperature in the range of 30° to 120° C., preferably 40° to 70° C., optionally by the use of a solvent, for a period in the range of 0.1 to 10 hours, and optionally subjecting the product of quaternization to salt exchange.

As specific examples of the tertiary amine represented by the general formula (5) used herein, trimethyl amine, triethyl amine, tripropyl amine, N-methyldiethanol amine, N,N-dimethyl-ethanol amine, triethanol amine, N,N-dimethyl-2-hydroxypropyl amine, N,N-dimethylbutyl amine, N,N-diethylmethyl amine, N,N-dimethylisopropyl amine, and N-methyldibutyl amine may be cited. As specific examples of the solvent, methanol, ethanol, isopropyl alcohol, and acetone may be cited.

In the method 2 of production, first the aminoester represented by the general formula (7) is obtained by subjecting the haloester of the general formula (4) obtained in the same manner as in the method 1 of production and the secondary amine represented by the general formula (6) used in an amount in the range of 0.9 to 5.0 times mol, preferably 0.95 to 2.0 times mol, per mol of the haloester at a temperature in the range of 0° to 90° C., preferably 30° to 70° C., optionally by the use of a water solvent, for a period in the range of 1 to 20 hours. Then, the quaternary ammonium salt (1) having the necessary counter ion can be obtained by quaternizing this aminoester of the general formula (7) with the quaternizing agent represented by the general formula (8) used in an amount in the range of 0.8 to 2.0 times mol, preferably 0.95 to 1.5 times mol, per mol of the aminoester at a temperature in the range of 70° to 120° C. for a period in the range of 0.5 to 10 hours in the absence or presence of a solvent until completion of the reaction, then aftertreating the product of quaternization as generally practiced, and optionally subjecting the product of aftertreatment to salt exchange by the use of an ion-exchange resin.

As specific examples of the secondary amine represented by the general formula (6) to be used herein, dimethyl amine, N-ethylmethyl amine, diethyl amine, N-methylisopropyl amine, N-ethylisopropyl amine, N-methylbutyl amine, diisopropyl amine, dipropyl amine, N-ethylbutyl amine, N-methylethanol amine, diethanol amine, N-methyl-2-hydroxypropyl amine, and di-(2-hydroxypropyl) amine may be cited. As specific examples of the quaternizer represented by the general formula (8), lower alkyl halides such as methyl chloride and di-lower alkyl sulfates such as dimethyl sulfate may be cited. The solvents which are usable for the quaternization include water, methanol, ethanol, isopropyl alcohol, and acetone, for example.

The composition of this invention for hair-treating agents can be used for hair rinse, hair conditioner, hair treatment, hair pack, hair cream, styling lotion, styling mousse, conditioning mousse, hair mousse, hair spray, shampoo, conditioning agent requiring no subsequent rinse, permanent or basic hair color, and permanent hair setting agent, for example.

For the hair-treating agents, one quaternary ammonium salt or a combination of two or more quaternary ammonium salts according to this invention can be used. The hair-treating agent incorporates therein the quaternary ammonium salt in an amount of not less than 0.1% by weight, preferably in the range of 0.1 to 20% by weight, and more preferably in the range of 0.1 to 10% by weight, based on the total amount of the composition of the agent.

In addition to the quaternary ammonium salt of this invention, the hair-treating agent of this invention can use oils and fats and silicones either singly or in the form of a combination of two or more members.

The oils and fats which are usable herein include such hydrocarbons as higher alcohols having a linear or branched alkyl group or alkenyl group, liquid paraffins, Vaseline (petrolatum), and solid paraffins, such lanolin derivatives as liquid lanolin and lanolin fatty acid, such oils and fats as higher fatty esters, higher fatty acids, and long-chain amide amines having an alkyl group or an alkenyl group, and such animal and plant oils and fats as mink oil and olive oil, for example. Among them, monoglycerides originating in saturated or unsaturated linear or branched fatty acids of 12 to 24 carbon atoms and higher alcohols and higher fatty acids having a linear or branched alkyl group or alkenyl group of 12 to 26 carbon atoms are preferable and fatty acid monoglycerides such as oleic monoglyceride, palmitic acid monoglyceride, behenic acid monoglyceride, and isostearic mono-glyceride, higher alcohols such as cetyl alcohol, stearyl alcohol, arachic alcohol, behenyl alcohol, carnaubyl alcohol, and celyl alcohol, and higher fatty acids such as stearic acid, myristic acid, behenic acid, isostearic acid, 18-methylicosanic acid, and coconut oil fatty acid are more preferable.

The silicones which are usable herein include various modified silicones such as amino-modified silicones and polyether-modified silicones in addition to dimethyl polysiloxane and methylphenyl polysiloxane, for example.

When such an oil or fat or a silicone is to be incorporated in the hair-treating agent, the amount thereof is appropriately not less than 0.01% by weight, preferably in the range of 0.01 to 30% by weight, and more preferably in the range of 0.05 to 20% by weight, based on the total amount of the composition of the agent.

Besides the components mentioned above, the hair-treating agent of this invention may optionally incorporate additionally therein such cationic active agents and nonionic active agents as the conventional mono- or di-(long-chain alkyl) quaternary ammonium salts, moisture-retaining agents such as glycerin and urea, macromolecular substances such as cationic polymers, poly-saccharides, and polypeptides, α-hydroxycarboxylic acids, aromatic sulfonic acids, pigments, perfumes, propellants, solvents, chelating agents, pH adjusting agents, and scurf-preventing agent in amounts not so large as to defeat the object of this invention.

The structure of the quaternary ammonium salt (1) of this invention can be confirmed by means of an infrared absorption spectrum or a nuclear-magnetic resonant spectrum.

The quaternary ammonium salt (1) of this invention is a novel surfactant usable as a softening basis which imparts excellent softness to fibers and exhibits great biodegradability. It is capable of imparting excellent softness and smoothness to hair and, therefore, applicable to such hair-treating agents as hair rinse and hair treatment, for example.

[Composition for softener composition]

The composition for the softener composition of this invention comprises 2 to 40% by weight, preferably 5 to 30% by weight, and more preferably 10 to 30% by weight, of the (A) component and the balance of water.

If the amount of the (A) component to be incorporated is less than 2% by weight, the softening effect desired by this invention will not be obtained. If this amount exceeds 40% by weight, the composition will increase in viscosity so much as to impair the handling property of the softener composition.

For the purpose of further improving the composition of this invention in softness and stability in storage, the composition can further incorporate therein the (B) component which is a linear or branched saturated or unsaturated alcohol of 8 to 44 carbon atoms. Appropriately, the amount of the (B) component to be incorporated is up to 20% by weight, preferably in the range of 1 to 10% by weight, based on the amount of the composition of the softener composition.

As specific examples of the linear or branched saturated or unsaturated alcohol of 8 to 44 carbon atoms, the following compounds may be cited. $CH_3(CH_2)_{11}OH$, $CH_3(CH_2)_{13}OH$, $CH_3(CH_2)_{15}OH$, $CH_3(CH_2)_{17}OH$, $CH_3(CH_2)_{19}OH$, $CH_3(CH_2)_{21}OH$, $CH_3(CH_2)_7CN=CH(CH_2)_8OH$ For the purpose of enhancing the softness and the stability in storage of the composition of the softener composition of this invention, the composition may incorporate therein the (C) component which is a linear or branched saturated or unsaturated fatty acid of 8 to 36 carbon atoms. Appropriately, the amount of the (C) component to be incorporated is up to 20% by weight, preferably in the range of 1 to 10% by weight, based on the amount of the composition of the softener composition.

As specific examples of the fatty acid of the (C) component usable herein, stearic acid, palmitic acid, myristic acid, lauric acid, captic acid, caprylic acid, oleic acid, isostearic acid, and alkyl-configuration fatty acids originating in such natural oils and fats as coconut oil, palm oil, beef tallow, rapeseed oil, and fish oil may be cited.

For the purpose of adjusting the viscosity of the composition and improving the stability of the composition in storage (as for prevention of gelation), the composition of this invention can further incorporate therein the (D) component which is a monovalent alcohol of 1 to 4 carbon atoms. The amount of the (D) component to be incorporated appropriately is up to 10% by weight, preferably in the range of 0.5 to 5% by weight, based on the amount of the composition of the softener composition.

As specific examples of the (D) component, i.e. the mono-valent alcohol of 1 to 4 carbon atoms, mentioned above, methyl alcohol, ethyl alcohol, propyl alcohol, isopropyl alcohol, and butyl alcohol may be cited.

If the (A) component has a high concentration in the composition of the softener composition of this invention, the composition will tend to increase in viscosity during storage. For the sake of repressing this trend of the composition toward an increase of viscosity, the composition appropriately incorporates therein the (E) component which is a polyether compound resulting from the alkoxylation of a compound having 3 or more active hydrogen atoms with ethylene oxide and optionally propylene oxide and/or trimethylene oxide to the polyether compound having a weight average molecular weight in the range of 5,000 to 2,000,000, and containing an oxyethylene group moiety in an amount of not less than 55% by weight based on the molecular weight or a derivative of the polyether compound.

As specific examples of the compound having 3 or more active hydrogen atoms and serving as the starting substance for the (E) component, polyhydric alcohols such as trimethylol propane, diethanol amine, triethanol amine, glycerin, penta-erythritol, sorbitol, saccharides, polyglycerin, polyvinyl alcohol, and partially saponified polyvinyl acetate, polyhydric phenols such as phenol resin and formalin condensates of alkyl phenols, and polyamine compounds such as ethylene diamine and diethylene triamine, triethylene tetramine, tetraethylene pentamine, pentaethylene hexamine, and other similar polyethylene imines may be cited. Further, the partially amidated compounds and N-alkylated compounds which are derived from these polyamine compounds can be used as the starting substance for the (E) component on the condition that they retain 3 or more active hydrogen atoms.

The (E) component is prepared by adding ethylene oxide and optionally propylene oxide and/or trimethylene oxide to a compound having three or more active hydrogen atoms as generally practiced. Advantageously, the (E) component is a sole adduct of ethylene oxide, a block adduct of ethylene oxide and propylene oxide, or a partially blocked adduct of ethylene oxide and propylene oxide. In the addition of two or more species of alkylene oxides to the compound having three or more active hydrogen atoms, the order in which the alkylene oxides are added is not critical. The order in which propylene oxide (hereinafter referred to briefly as "PO") is added before ethylene oxide (hereinafter referred to briefly as "EO") is nevertheless advantageous in respect that the composition of this invention containing the (A) component at a high concentration is more effectively precluded from an increase in viscosity during storage.

The molecular weight of the (E) component is proper in the range of 5,000 to 2,000,000, preferably 10,000 to 100,000. The proportion of the moiety of the oxyethylene (EO chain) group to the molecule properly is not less than 55% by weight, preferably not less than 80% by weight, based on the total molecular weight.

If the molecular weight of the (E) component in this case is less than 5,000, the trend of the composition of the softener composition toward an increase in viscosity during storage will not be effective to any substantial effect. Conversely, if the molecular weight exceeds 2,000,000, the viscosity of the composition of the softener composition will notably increase possibly to the extent that disadvantageously the agent may not be easily extracted from a bottle containing it.

If the proportion of the oxyethylene group to the molecular weight of the (E) component (based on the total weight) is less than 55% by weight, the effect of repressing the trend of the composition of the softener composition toward an increase of viscosity during storage will be low.

As specific examples of the derivative of the aforementioned polyether compound as the (E) component, the cross-linked products obtained by the reaction of the aforementioned polyether compound with compounds possessed of an isocyanate group, the derivatives of the aforementioned polyether compound produced by having the terminal hydroxyl group of the compound sulfated, phosphated, carboxyalkylated, or fatty acid esterified, and the derivatives of the aforementioned polyether compound obtained by having part of the nitrogen atom of the compound converted into a cation may be cited. Among them, the products of esterification of fatty acids and the products of conversion into a cation offer an appropriate choice.

The fatty acid to be used in the manufacture of the product of esterification of a fatty acid appropriately is of a species having 7 to 23 carbon atoms. Such factors as the number of double bonds and the presence or absence of a branch in the molecular structure do not appreciably affect the quality of the fatty acid.

As specific examples of the product obtained by conversion into a cation, the derivatives of the polyether compound obtained by converting part of the nitrogen atom of the compound into a cation by the use of a dialkyl sulfuric acid or a halogenated alkyl and the derivatives obtained by neutralizing the products resulting from the conversion into a cation as with acetic acid or an alkylbenzene sulfonic acid may be cited.

The amount of the (E) component incorporated in the composition of the softener composition of this invention appropriately is in the range of 0.5 to 5% by weight, preferably 1 to 3% by weight, based on the total weight of the composition. The weight ratio of the (E) component to the (A) component. [(E) component]:[the (A) component], appropriately in the range of 1/100 to 1/2.5, preferably 1/50 to 1/5. The total content if the (A) component and the (E) component in the composition of the softener composition of this invention is appropriate in the range of 3 to 45% by weight, preferably 11 to 39% by weight, and more preferably 14 to 32% by weight, based on the total weight of the composition. So long as the amount of the (E) component is in the range mentioned above, the composition of the softener composition of this invention manifests the softening capacity at the level desired by this invention and, at the same time, precludes the trend of its own toward an increase in viscosity during storage.

As specific examples of the nonionic surfactant to be used as the (F) component herein, adduct of 20 to 30 mols of ethylene oxide to $C_{12}$–$C_{14}$ alcohol, for example, Emulgen 120, Emulgen 130 and adduct of 20 to 30 mols of ethylene oxide to satulated or unsatulated $C_{18}$ alcohol, for example, Emulgen 430 produced by Kao Corporation and adduct of 20 to 30 mols of ethylene oxide to $C_{12}$–$C_{14}$ secondary alcohol, for example, Softanol 200 and Softanol 300 produced by Nippon Shokubai Kagaku Kogyo Co., Ltd. may be cited.

The composition of this invention can incorporate, as a basis for the softener composition, a known cation compound (such as quaternary ammonium salt or imidazolinium salt), an ester or an amide, or a mixture of two or more such compounds. As concrete examples of the basis usable herein, the quaternary ammonium salts represented by the following general formula (IX) and the compounds represented by the following general formulas (X-1) to (X-8).

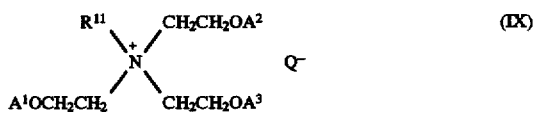

(IX)

[wherein $R^{11}$ is an alkyl or hydroxyalkyl group of 1 to 4 carbon atoms, $A^1$, $A^2$, and $A^3$ are the same or different from each and are a hydrogen atom or $R^{12}CO$— (wherein $R^{12}$ is a linear or branched alkyl or alkenyl group of 7 to 35 carbon atoms), providing that at least one of $A^1$, $A^2$, and $A^3$ is a group represented by $R^{12}CO$— (wherein $R^{12}$ has the same meaning as defined above) and $Q^-$ is an anion group]. As concrete examples of $Q^-$, halogen ions such as $Cl^-$ and $Br^-$ and alkyl sulfate groups of 1 to 5 carbon atoms may be cited.

In the composition of this invention, the moiety $Q^-$ used in the quaternary ammonium salt represented by the general formula (IX) may be identical or not identical with the moiety $X^-$ used simultaneously in the quaternary ammonium salt (I).

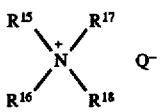 (X-1)

[wherein $R^{15}$ and $R^{16}$ are the same or different from each other and are a linear or branched alkyl, alkenyl, or 2-hydroxyalkyl group of 10 to 24 carbon atoms, $R^{17}$ is an alkyl or hydroxyalkyl group of 1 to 3 carbon atoms, benzyl group, or a group represented by the general formula, —(C$_2$H$_3$O)$_p$H, (wherein P is a number in the range of 1 to 3), $R^{18}$ is a hydrogen atom, an alkyl or hydroxy-alkyl group of one to three carbon atoms, benzyl group, or a group represented by the general formula, —(C$_2$H$_4$O)$_p$H (wherein p has the same meaning as defined above) and Q$^-$ has the same meaning as defined above].

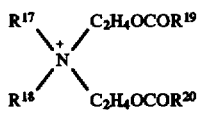 (X-2)

[wherein $R^{17}$, $R^{18}$, and Q$^-$ have the same meanings as defined above, $R^{19}$ and $R^{20}$ are the same or different from each other and are a linear or branched alkyl, alkenyl, or 2-hydroxyalkyl group of 9 to 23 carbon atoms]

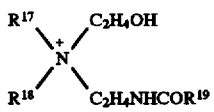 (X-3)

[wherein $R^{17}$, $R^{18}$, $R^{19}$, and Q$^-$ have the same meanings as defined above].

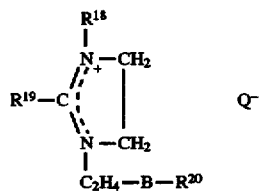 (X-4)

[wherein $R^{18}$, $R^{19}$, $R^{20}$, and Q$^-$ have the same meanings as defined above and B is a group represented by the formula, —OCO— or —NHCO—].

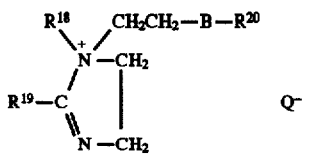 (X-5)

[wherein $R^{18}$, $R^{19}$, $R^{20}$, B, and Q$^-$ have the same meanings as defined above].

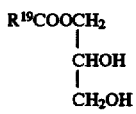 (X-6)

[wherein $R^{19}$ has the same meaning as defined above].

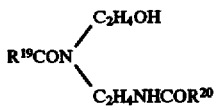 (X-7)

[wherein $R^{19}$ and $R^{20}$ have the same meanings as defined above].

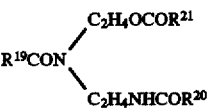 (X-8)

[wherein $R^{19}$ and $R^{20}$ has the same meaning as defined above and $R^{21}$ is an alkyl, alkenyl, or 2-hydroxyalkyl group of 9 to 23 carbon atoms].

The composition of this invention can incorporate therein such an inorganic electrolyte as NaCl, CaCl$_2$, MgCl$_2$, NaNO$_3$, NaNO$_2$, Na$_2$SO$_4$, MgSO$_4$, or CaSO$_4$ in order to adjust its viscosity. The amount of the inorganic electrolyte to be incorporated in the composition in this case is appropriate in the range of 0 to 2% by weight, preferably 0 to 1% by weight, based on the weight of the composition.

The composition of the softener composition of this invention can further incorporate therein an acidic or an alkaline substance for the adjustment of the pH value thereof. From the viewpoint of the viscosity and the stability in storage of the composition, It is advantageous to add the acidic or alkaline substance in an amount such that the pH value of the composition of this invention falls in the range of 1.5 to 6.5.

The composition of the softener composition of this invention exhibits high stability continuously even when It is stored for a long time. For the purpose of ensuring the composition retaining the high stability while in storage under severe conditions, the composition may appropriately incorporate therein a hydrotropic agent such as ethylene glycol, glycerin, propylene glycol, or urea, etc.

The composition of this invention can further incorporate therein a pigment or a dye for improving the appearance thereof, a silicone for precluding the occurrence of foam during the course of rinsing, or perfume for enhancing the touch during use or after finish. A bactericide can also be incorporate therein.

One typical method for the preparation of the composition of the softener composition of this invention will be described below. The preparation of the composition of this invention is not limited to this particular method.

An emulsion is prepared by dissolving the (A) component or the mixture of the (A) component with other components (except the (E) component) and gradually adding the resultant melt dropwise into deionized water kept stirred at 60° C. Then, the (E) component may be optionally added into the resultant emulsion. The aqueous solution of a nonionic surfactant may be used in the place of the deionized water. After the (A) to (E) components have been added to the emulsion, the produced mixture may incorporate therein an inorganic salt for adjusting the viscosity of the composition.

The composition of the softener composition of this invention imparts ample softness and eminent elasticity to various kinds of fibers and, at the same time, evinces highly satisfactory stability (ability to preclude gelation or increase of viscosity while in storage and ability to prevent the softener composition from hydrolyzing while in storage).

The glycerol compound (2), which serves as the starting raw material for the quaternary ammonium salt (1) of this invention is produced by the well-known method. It is known to by-produce a large-number met in the course of the production. In this invention, the produced compound (2) may be purified by removing such a large-number mer. The compound containing the large-number met at a concentration of not more than 50% by weight based on the total weight of the compound, however, can be safely used in its unmodified form as the starting raw material.

The glycerol compound (2), is generally produced by a process of glycel etherifying epichlorohydrin with alcohol of an amount in the range of 1.5 to 20 times mol, preferably 2 to 10 times mol, per mol of the epichlorohydrin in the presence of an alkali catalyst at a temperature in the range of 40° to 100° C.

The alcohols which are usable for the etherification herein include dodecyl alcohol, tetradecyl alcohol, hexadecyl alcohol, octadecyl alcohol, eicosyl alcohol, docosyl alcohol, oleyl alcohol, beef tallow alcohol, palm stearin alcohol, and mixtures thereof, for example.

The alkali catalysts which are usable in this invention include sodium hydroxide, potassium hydroxide, sodium methylate, and sodium ethylate, for example.

Further, the composition of this invention can incorporate therein any of the compounds represented by the general formulas (III-1) to (III-7) as a (G) component for the purpose of improving the softness of the composition and any of the compounds represented by the general formulas (IV-1) to (IV-9) as a (H) component for the purpose of enhancing the stability in storage.

(G) component:

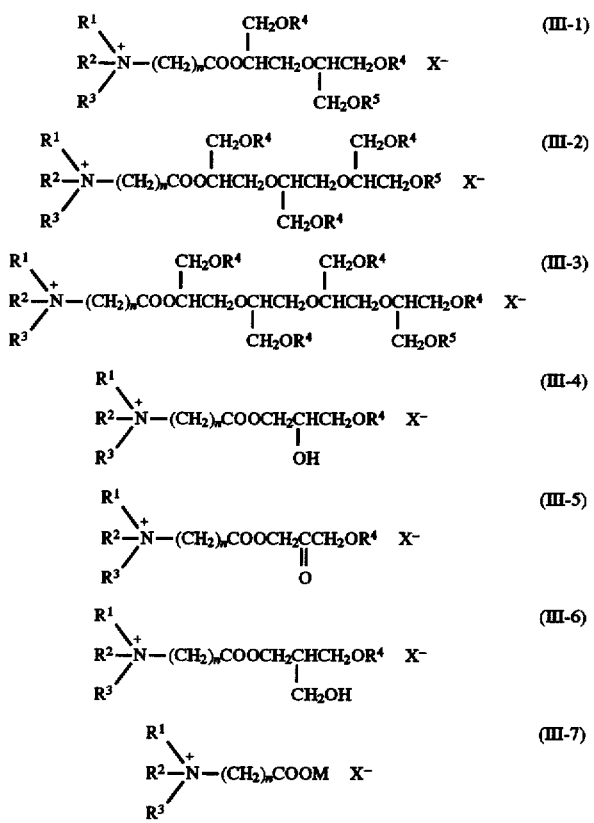

[wherein $R^1$, $R^2$, $R^3$, $R^4$, $R^5$, $X^-$, and n have the same meanings as defined above and M is a hydrogen atom or a cation group].

(H) component:

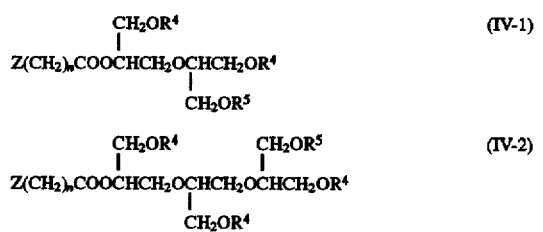

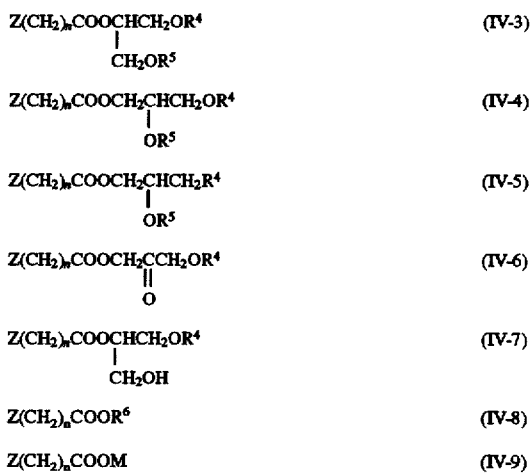

[wherein $R^4$, $R^5$, n, and M have the same meanings as defined above, $R^6$ is an alkyl group or an alkenyl group of 1 to 22 carbon atoms, and Z is a halogen atom].

As the (G) component, any of the compounds represented by the general formulas (III-1) to (III-7), preferably the compounds represented by the general formulas (III-1) to (III-3), and particularly preferably the compounds represented by the general formulas (III-1) and (III-2). As specific examples of the ($R^1$, $R^2$, and $R^3$) set in these general formulas, (methyl group, methyl group, and methyl group), (ethyl group, ethyl group, and ethyl group), (methyl group, methyl group, and hydroxyethyl group), (methyl group, methyl group, and ethyl group), and (hydroxyethyl group, hydroxyethyl group, and hydroxy-ethyl group) may be cited. Among other sets of groups mentioned above, the sets of (methyl group, methyl group, and methyl group), (ethyl group, ethyl group, and ethyl group), etc. prove particularly advantageous.

As specific examples of $R^4$ and $R^5$, decyl group, dodecyl group, tetradecyl group, hexadecyl group, octadecyl group, etc. may be cited. Among them, the hexadecyl group, octadecyl group, etc. are particularly advantageous. n is an integer in the range of 1 to 6, preferably 1 to 3. More appropriately, n is 1.

As preferred examples of $X^-$, $Cl^-$, $Br^-$, $HCO_3^-$, and $CH_3SO_4^-$, may be cited. $Cl^-$ is more preferably.

As preferred examples of M, H, Na, K, etc. may be cited.

As the (H) component, any of the compounds represented by the general formulas (IV-1) to (IV-9), preferably the compounds represented by the general formulas (IV-1) to (IV-4), and particularly preferably the compounds represented by the general formulas (IV-1) and (IV-2). As specific examples of $R^4$ and $R^5$ in these formulas, decyl group, dodecyl group, tetradecyl group, hexadecyl group, octadecyl group, etc. may be cited. Distinct hexadecyl group, octadecyl group, etc. are more preferable. n is an integer in the range of 1 to 6, preferably 1 to 3. More appropriately, n is 1. As preferred examples of Z, Cl, B, etc. may be cited.

As preferred examples of the compound of the general formula (IV-8) to be used as the (H) component, methyl chloroacetate, ethyl chloroacetate, n-butyl chloroacetate, isopropyl chloro-acetate, t-butyl chloroacetate, methyl bromoacetate, ethyl bromoacetate, etc. may be cited. Among them, methyl chloroacetate and ethyl chloroacetate prove particularly advantageous.

As preferred examples of the compound of the general formula (IV-9) to be used as the (H) component, $ClCH_2COOM$, $ClC_2H_4COOM$, $ClC_3H_6COOM$, $ClC_4H_8COOM$, $ClC_5H_{10}COOM$, $BrCH_2COOM$, $BrC_2H_4COOM$, etc. may be cited. And $ClCH_2COOM$ is more preferable. As preferred example of M, the alkali metals and the alkaline earth metals in the Periodic Table of the Elements, cation groups selected from the group consisting of alkaline earth metals and transition metals, amine salts of 1 to 10 carbon atoms, and quaternary ammonium salts may be cited. Specifically, alkali metal salts, alkaline earth metal salts, amine salts of 1 to 6 carbon atoms (such as, for example, monoethanol amine salt, diethanol amine salt, and triethanol amine salt), and quaternary ammonium salts offer an appropriate choice.

When the composition of this invention incorporates the (G) component therein, the amount of the (G) component to be used is appropriately such that the weight ratio of [(G) component]:[(A) component+(G) component] is not more than 20/80. The amount of the (G) component to be incorporated in the composition is such that the total content of the (A) component and the (G) component is in the range of 3 to 40% by weight.

When the composition of this invention incorporates the (H) component therein, the amount of the (G) component to be used is appropriately such that the weight ratio of [(D) component]:[(A) component+(G) component+(H) component] is not more than 20/80. The amount of the (H) component to be incorporated in the composition is such that the total content of the (A) component, the (G) component, and the (H) component is in the range of 3 to 40% by weight.

When the composition incorporates the (G) component, the (H) component, and such optional components as non-ionic surfactant, these components may be mixed in advance with the (A) component and water. Otherwise, they may be added separately.

When these components are solid at normal room temperature or they have a high viscosity, they may be incorporated heated or melted into the composition for the purpose of improving their handling property.

The composition of the softener composition of the present invention imparts ample softness and elasticity (sensation of fluffiness) to various kinds of fibers and, at the same time, enjoys highly satisfactory stability (ability to preclude gelation or increase of viscosity while in storage and ability to prevent the softener composition from hydrolyzing while in storage).

EXAMPLES

Now, this invention will be described more specifically below with reference to examples. It should be noted, however, that this invention is not limited to these examples.

Example 1-1

In a four-neck flask provided with a stirrer, a thermometer, and a condenser, 177.6 g of 1,3-dioctadecanoxy-2-propanol and 38 g of monochloroacetic acid were placed and heated to 140° C. They were reacted at that temperature for 7 hours while the formed water was removed by distillation. The reaction mixture obtained thereby was washed with water to remove the excess monochloroacetic acid and to obtain 200 g of a corresponding chloroacetic ester.

Then, in an autoclave provided with a stirrer and a thermo-meter, 150 g of the chloroacetic ester, 16 g of trimethyl amine, and 40 g of isopropyl alcohol were placed and reacted therein at 60° C. for four hours. After the reaction, the reaction solution was crystallized with acetone and the crystals were dried to obtain 150 g of a white powder as a desired product.

The white powder was found to have the following structure by the NMR spectrum and the IR spectrum.

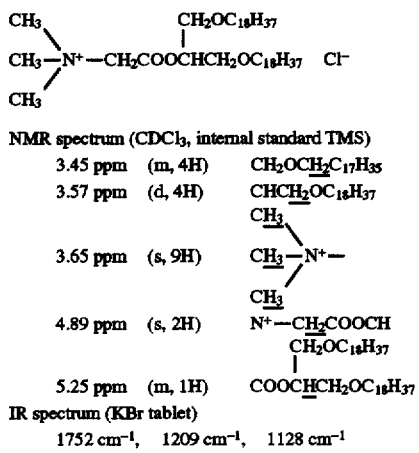

Example 1-2

In a four-neck flask provided with a stirrer, a thermometer, and a condenser, 177.6 g of 1,3-dioctadecanoxy-2-propanol and 46 g of monochlorobutyric acid were placed and heated to 140° C. They were reacted at that temperature for 7 hours while the formed water was removed by distillation. The reaction mixture obtained thereby was washed with water to remove the excess monochloroacetic acid and to obtain 210 g of a corresponding chlorobutyric ester.

Then, in an autoclave provided with a stirrer and a thermo-meter, 150 g of the chlorobutyric ester, 15 g of trimethyl amine, and 40 g of isopropyl alcohol were placed and reacted therein at 80° C. for 4 hours. After the reaction, the reaction solution was crystallized with acetone and the crystals were dried to obtain 150 g of a white powder as a desired product.

The white powder was found to have the following structure by the NMR spectrum and the IR spectrum.

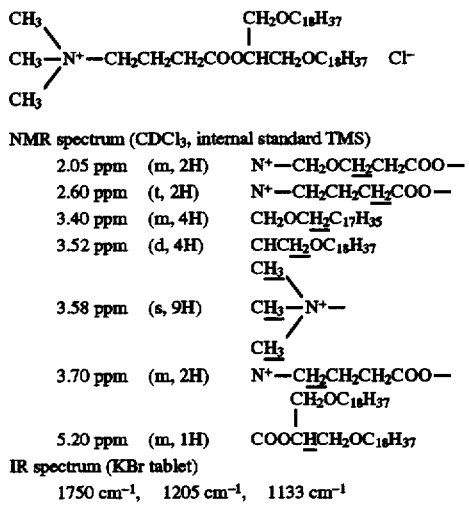

Example 1-3

In a four-neck flask provided with a stirrer, a thermometer, and a condenser, 177.6 g of 1,3-dioctadecanoxy-2-propanol and 45 g of monochlorohexanoic acid were placed and heated to 140° C. They were reacted at that temperature for 7 hours while the formed water was removed by distillation to obtain 220 g of a corresponding chlorohexanic ester.

Then, in an autoclave provided with a stirrer and a thermo-meter, 150 g of the chlorohexanic ester, 14 g of trimethyl amine, and 60 g of ethanol were placed and reacted therein at 80° C. for 4 hours. After the reaction, the reaction solution was crystallized with acetone and the crystals were dried to obtain 150 g of a white powder as a desired product.

The white powder was found to have the following structure by the NMR spectrum and the IR spectrum.

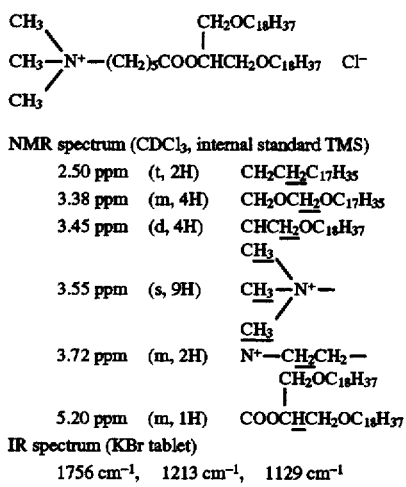

NMR spectrum (CDCl$_3$, internal standard TMS)

| | | |
|---|---|---|
| 2.50 ppm | (t, 2H) | CH$_2$C$\underline{H}_2$C$_{17}$H$_{35}$ |
| 3.38 ppm | (m, 4H) | CH$_2$OC$\underline{H}_2$OC$_{17}$H$_{35}$ |
| 3.45 ppm | (d, 4H) | C$\underline{H}$CH$_2$OC$_{18}$H$_{37}$ |
| 3.55 ppm | (s, 9H) | C$\underline{H}_3$—N$^+$— / CH$_3$ |
| 3.72 ppm | (m, 2H) | N$^+$—C$\underline{H}_2$CH$_2$— CH$_2$OC$_{18}$H$_{37}$ |
| 5.20 ppm | (m, 1H) | COOC$\underline{H}$CH$_2$OC$_{18}$H$_{37}$ |

IR spectrum (KBr tablet)
1756 cm$^{-1}$, 1213 cm$^{-1}$, 1129 cm$^{-1}$

Example 1-4

In a four-neck flask provided with a stirrer, a thermometer, and a condenser, 167 g of chloroacetic ester obtained in the same manner as in Example 1-1, 56 g of an aqueous 50% dimethyl amine solution, and 90 g of deionized water were placed and heated to 50° C. They were stirred at that temperature for 12 hours and then washed with water to remove the excess dimethyl amine and to obtain 165 g of a corresponding amino ester.

Then, in an autoclave provided with a stirrer and a thermo-meter, 120 g of the amino ester, 12 g of methyl chloride, and 80 g of acetone were placed and reacted therein at 90° C. for 6 hours. After the reaction, the reaction solution was crystallized with acetone and the crystals were dried to obtain 100 g of a white powder as a desired product.

The white powder was found to have the following structure, identical to that of the product synthesized in Example 1-1, by the NMR spectrum and the IR spectrum.

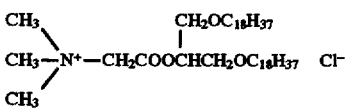

Example 1-5

In a four-neck flask provided with a stirrer, a thermometer, and a condenser, 243.6 g of an adduct of 5 mols of ethylene oxide to 1,3-dioctadecanoxy-2-propanol [hydroxyl group value 69 (KOH mg/g)] and 38 g of monochloroacetic acid were placed and heated to 140° C. They were reacted at that temperature for 7 hours while the formed water was removed by distillation. The reaction mixture consequently obtained thereby was washed with water to remove the excess monochloroacetic acid and to obtain 270 g of a corresponding chloroacetic ester.

Then, in an autoclave provided with a stirrer and a thermo-meter, 150 g of the chloroacetic ester, 13 g of trimethyl amine, and 40 g of isopropyl alcohol were placed and reacted therein at 60° C. for 4 hours. After the reaction, the reaction solution was crystallized with acetone and the crystals were dried to obtain 120 g of a light yellow gel as a target product.

The light yellow gel was found to have the following structure by the NMR spectrum and the IR spectrum.

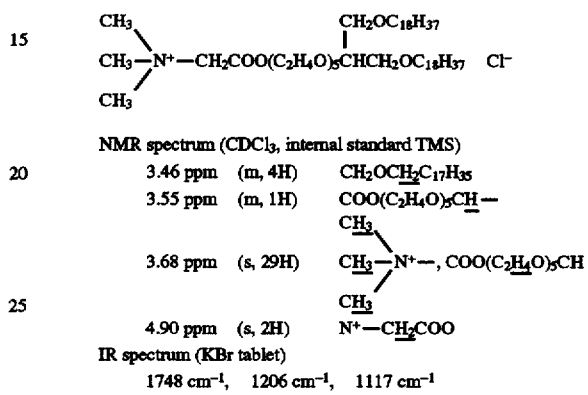

NMR spectrum (CDCl$_3$, internal standard TMS)

| | | |
|---|---|---|
| 3.46 ppm | (m, 4H) | CH$_2$OC$\underline{H}_2$C$_{17}$H$_{35}$ |
| 3.55 ppm | (m, 1H) | COO(C$_2$H$_4$O)$_5$C$\underline{H}$— C$\underline{H}_3$ |
| 3.68 ppm | (s, 29H) | C$\underline{H}_3$—N$^+$—, COO(C$_2$$\underline{H}_4$O)$_5$CH / CH$_3$ |
| 4.90 ppm | (s, 2H) | N$^+$—C$\underline{H}_2$COO |

IR spectrum (KBr tablet)
1748 cm$^{-1}$, 1206 cm$^{-1}$, 1117 cm$^{-1}$

Wherever % is mentioned, it is % by weight unless otherwise specified.

Examples 2-1 to 2-23 and Comparative Experiments 2-1 to 2-11

Liquid compositions of softener composition indicated in Tables 2-8 to 2-10 were prepared with the (A) components shown in Table 2-1, the (B) components shown in Table 2-2, the (C) components shown in Table 2-3, the (D) components shown in Table 2-4, the (E) components shown in Table 2-5, the (F) components shown in Table 2-6, and other components shown in Table 2-7. These compositions were tested for softness, elasticity, and stability in storage by the methods described below. The results are shown in Tables 2-8 to 2-10.

The compositions invariably contained 0.2% by weight of CaCl$_2$, the balance being water after adding an optional component and had the pH value adjusted to 3.0 with an aqueous HCl solution.

(1) Evaluation for softness and elasticity:

Commercially available cotton towel, acrylic fibers, and polyester fibers were washed five times with a commercially available detergent (produced by Kao Soap Co., Ltd. and marketed under trademark designation of "Attack") and then rinsed to remove excess detergent. The fabrics and a sample liquid composition added thereto in an amount of 0.5% by weight, based on the weight of fabric, were stirred at 25° C. at a bath ratio of 1/30 for three minutes. Then, the fabrics were left drying in a current of air indoors and then left standing in a constant temperature constant humidity chamber at 20° C. and 65% RH for 24 hours.

The fabrics were tested for softness and elasticity.

The softness and the elasticity were determined by comparing the fabrics under test with the fabrics treated with a composition of softener composition of Comparative Experiment 2-1 and rating the results of comparison on the five-point scale wherein:

+2: Higher softness or elasticity than control.
+1: Slightly higher softness or elasticity than control.
0: Softness or elasticity equal to that of control.
−1: Control slightly higher softness or elasticity than sample.
−2: Control higher softness or elasticity than sample.

(2) Test for stability in storage:

The liquid compositions of softener composition prepared as described above were tightly sealed, stored at 20° C. and 40° C. for 20 days and, at the end of the storage, visually examined as held in a tightly sealed state with respect to appearance and flowability. The samples showing no discernible change in appearance and flowability were rated as satisfactory and those showing a change in state were reported as defective due to the change.

Example 2-24

Hair rinse:

A hair rinse of the following composition was prepared.

| (Ingredient) | (% by weight) |
|---|---|
| Quaternary ammonium salt (Example 1) | 1.0 |
| Cetyl alcohol | 3.0 |
| Behenic acid | 1.0 |
| Diethylene glycol monoethyl ether | 3.0 |
| Hydroxyethyl cellulose | 0.5 |
| Water | 91.1 |
| Perfume | 0.4 |
| | 100.0 |

Styling lotion:

A styling lotion of the following composition was prepared.

| (Ingredient) | (% by weight) |
|---|---|
| Quaternary ammonium salt (Example 2) | 0.5 |
| polyethylene glycol | 0.5 |
| Alkanol amine solution of acrylic resin | 5.0 |
| 2-Benzyloxy ethanol | 1.0 |
| Methacryl ester polymer | 1.0 |
| Ethanol | 20.0 |
| Perfume | 0.4 |
| Water | Balance |
| | 100.0 |

Conditioning foam:

A conditioning foam of the following composition was prepared.

| (Ingredient) | (% by weight) |
|---|---|
| Quaternary ammonium salt (Example 3) | 0.5 |
| Octyldodecyl myristate | 1.0 |
| Dipropylene glycol | 1.0 |
| Glycerin | 2.5 |
| Liquid paraffin | 2.5 |
| Polyoxyethylene (20) sorbitan monostearate | 0.2 |
| Glycolic acid | 0.5 |
| Adduct of 1 mol of isostearyl pentaerythritol glycidyl ether | 0.5 |
| Ethanol | 5.0 |
| Methylparaben | 0.1 |
| Perfume | 0.1 |
| Propellant (LPG) | 10.0 |
| Water | Balance |
| | 100 |

TABLE 2-1

| | (A) Component | |
|---|---|---|
| A-1 | $CH_3\text{\textbackslash}$<br>$CH_3-N^+-CH_2COOCHCH_2OR/Cl^-$<br>$CH_3/\quad\quad\quad\quad\quad\quad CH_2OR$ | R: Alkyl group originating in beef tallow |
| A-2 | $CH_3\text{\textbackslash}$<br>$CH_3-N^+-CH_2COOCHCH_2OR/Cl^-$<br>$CH_3/\quad\quad\quad\quad\quad\quad CH_2OR$ | R: Alkyl group originating in palm stearic acid |
| A-3 | $CH_3\text{\textbackslash}$<br>$CH_3-N^+-CH_2COOCHCH_2OR/CH_3SO_4^-$<br>$CH_3/\quad\quad\quad\quad\quad\quad CH_2OR$ | R: Alkyl group originating in beef tallow |
| A-4 | $CH_3\text{\textbackslash}$<br>$CH_3-N^+-CH_2COOCHCH_2OR/C_2H_5SO_4^-$<br>$CH_3/\quad\quad\quad\quad\quad\quad CH_2OR$ | R: Alkyl group originating in palm stearic acid |
| A-5 | $CH_3\text{\textbackslash}$<br>$CH_3-N^+-CH_2COOCHCH_2OR/Cl^-$<br>$CH_3/\quad\quad\quad\quad\quad\quad CH_2OR$ | R: Alkyl group originating in coconut oil |
| A-6 | $C_2H_5\text{\textbackslash}$<br>$C_2H_5-N^+-CH_2COOCHCH_2OR/Cl^-$<br>$C_2H_5/\quad\quad\quad\quad\quad\quad CH_2OR$ | R: Alkyl group originating in beef tallow |

TABLE 2-2

| | (B) Component |
|---|---|
| B-1 | $CH_3(CH_2)_{11}OH$ |
| B-2 | $CH_3(CH_2)_{15}OH$ |
| B-3 | $CH_3(CH_2)_{17}OH$ |
| B-4 | $CH_3(CH_2)_7CH=CH(CH_2)_8OH$ |

TABLE 2-3

| | (C) Component |
|---|---|
| C-1 | Beef tallow fatty acid |
| C-2 | Palm stearic acid |
| C-3 | Oleic acid |

TABLE 2-4

| | (D) Component |
|---|---|
| D-1 | Isopropyl alcohol |
| D-2 | Ethyl alcohol |

TABLE 2-5

| | (E) Component |
|---|---|
| E-1 | EO additive of glycerin (MW 8,900) |
| E-2 | PO/EO = 15/85 additive of glycerin (MW 10,000) |
| E-3 | PO/EO = 10/90 additive of sorbitol (MW 15,000) |
| E-4 | PO/EO = 2/98 additive of tetraethylene pentamine (MW 20,000) |
| E-5 | PO/EO = 5/95 additive of polyethylene imine (MW 300,000) |

TABLE 2-6

| | (F) Component |
|---|---|
| F-1 | Polyoxyethylene (20 mols) lauryl ether |
| F-2 | Polyoxyethylene (30 mols) oleyl ether |
| F-3 | Polyoxyethylene (20 mols) stearyl ether |

TABLE 2-7

| | Other component | |
|---|---|---|
| G-1 | $\begin{array}{c} CH_3 \\ CH_3-N^+-CH_2COOCHCH_2OCHCH_2OR/Cl^- \\ CH_3 \end{array}$ with $CH_2OR$ and $CH_2OR$ substituents | R: Alkyl group originating in beef tallow |
| G-2 | $CH_3{-}N^+({-}CH_3)({-}CH_3){-}CH_2COOCHCH_2OCHCH_2OR/CH_3SO_4^-$ with $CH_2OR$, $CH_2OR$ | R: Alkyl group originating in palm stearic acid |
| G-3 | $CH_3{-}N^+({-}CH_3)({-}CH_3){-}CH_2COOCHCH_2OCHCH_2OR/C_2H_5SO_4^-$ with $CH_2OR$, $CH_2OR$ | R: Alkyl group originating in beef tallow |
| G-4 | $CH_3{-}N^+({-}CH_3)({-}CH_3){-}CH_2COOCHCH_2OCHCH_2OCHCH_2OR/Cl^-$ with $CH_2OR$, $CH_2OR$, $CH_3OR$ | R: Alkyl group originating in beef tallow acid |
| G-5 | $C_2H_5{-}N^+({-}C_2H_5)({-}C_2H_5){-}CH_2COOCHCH_2OCHCH_2OR/Cl^-$ with $CH_2OR$, $CH_2OR$ | R: Alkyl group originating in coconut oil |
| G-6 | $CH_3{-}N^+({-}CH_3)({-}CH_3){-}CH_2COOCHCH_2OCHCH_2OR/Cl^-$ with $CH_2OR$, $CH_2OR$ | R: Alkyl group originating in palm stearic acid |
| G-7 | $HOC_2H_4{-}N^+({-}HOC_2H_4)({-}C_2H_5){-}CH_2COOCH_2CHCH_2OR$ $Cl^-$ with $OH$ | R: Alkyl group originating in beef tallow |
| G-8 | $C_2H_5{-}N^+({-}C_2H_5)({-}C_2H_5){-}(CH_2)_3COOCH_2CCH_3OR$ $CH_3SO_4^-$ with $=O$ | R: Alkyl group originating in palm stearic acid |
| G-9 | $HOC_2H_4{-}N^+({-}HOC_2H_4)({-}HOC_2H_4){-}CH_3COOCHCH_2OR$ $Cl^-$ with $CH_2OH$ | R: Alkyl group originating in beef tallow |
| G-10 | $CH_3{-}N^+({-}CH_3)({-}CH_3){-}CH_2COOH$ $Cl^-$ | |

TABLE 2-7-continued

| | Other component |
|---|---|
| H-1 | $\begin{array}{c}CH_2OC_{18}H_{37}\\|\\ClCH_2COOCHCH_2OCHCH_2OC_{18}H_{37}\\|\\CH_2OC_{16}H_{33}\end{array}$ |
| H-2 | $\begin{array}{c}CH_2OC_{18}H_{37}\quad CH_2OC_{18}H_{37}\\|\qquad\qquad\quad|\\Cl(CH_2)_3COOCHCH_2CHCH_2OCHCH_2OC_{16}H_{33}\\|\\CH_2OC_{18}H_{37}\end{array}$ |
| H-3 | $\begin{array}{c}ClCH_2COOCHCH_2OC_{18}H_{37}\\|\\CH_2OC_{18}H_{37}\end{array}$ |
| H-4 | $\begin{array}{c}ClCH_2COOCH_2CHCH_2OC_{16}H_{33}\\|\\C_{18}H_{37}\end{array}$ |
| H-5 | $\begin{array}{c}ClCH_2COOCH_2CHCH_2OC_{18}H_{37}\\|\\OH\end{array}$ |
| H-6 | $\begin{array}{c}Cl(CH_2)_3COOCH_2CCH_2OC_{16}H_{13}\\\|\|\\O\end{array}$ |
| H-7 | $\begin{array}{c}ClCH_2COOCHCH_2OC_{18}H_{37}\\|\\CH_2OH\end{array}$ |
| H-8 | Methyl chloroacetate |
| H-9 | $ClCH_2COONa$ |

TABLE 2-8

| | Composition for soft-finishing agent | | | | | | | | | Stability in storage | |
|---|---|---|---|---|---|---|---|---|---|---|---|
| | (A) component | (B) component | (C) component | (D) component | (E) component | (F) component | Other component | Soft-ness | Elastic-ity | 20° C. | 40° C. |
| Examples | | | | | | | | | | | |
| 2-1 | A-1 (15) | B-1 (1.0) | C-1 (1.5) | D-1 (2.5) | — | F-1 (2.0) | G-1(1.5) G-4(0.2) | '+2 | '+2 | o | o |
| 2-2 | A-1 (15) | — | C-3 (1.5) | D-2 (3.0) | — | F-1 (2.0) | — | '+2 | '+2 | o | o |
| 2-3 | A-1 (15) | — | C-1 (1.0) | — | E-1 (1.0) | F-2 (2.0) | G-1(1.5) H-2(0.8) | '+2 | '+2 | o | o |
| 2-4 | A-1 (15) | B-4 (1.5) | — | D-1 (2.5) | E-1 (1.0) | F-1 (2.0) | G-2(1.0) | '+2 | '+2 | o | o |
| 2-5 | A-1 (15) | B-1 (1.5) | C-2 (2.0) | — | — | — | H-4(1.0) | '+1 | '+2 | o | o |
| 2-6 | A-1 (15) | — | — | D-1 (2.5) | E-2 (1.0) | — | G-3(1.0) | '+2 | '+2 | o | o |
| 2-7 | A-1 (15) | — | — | — | — | F-3 (2.0) | G-4(1.0) | '+2 | '+2 | o | o |
| 2-8 | A-1 (20) | B-3 (1.5) | C-3 (2.5) | D-1 (2.5) | E-4 (1.0) | F-1 (2.0) | H-3(1.5) H-9(0.8) | '+2 | '+2 | o | o |
| 2-9 | A-1 (20) | — | C-1 (5.0) | D-2 (3.0) | — | — | G-5(1.0) H-1(0.5) | '+2 | '+2 | o | o |
| 2-10 | A-2 (15) | — | C-2 (5.0) | D-1 (2.5) | E-3 (1.0) | — | G-8(1.0) | '+1 | '+2 | o | o |
| 2-11 | A-2 (15) | B-2 (1.5) | — | — | — | F-3 (2.0) | G-9(1.2) H-5(0.5) | '+2 | '+2 | o | o |
| 2-12 | A-2 (15) | — | C-1 (5.0) | D-2 (2.5) | — | F-1 (2.0) | G-6(1.5) | '+1 | '+2 | o | o |

TABLE 2-9

| | Composition for soft-finishing agent | | | | | | | | | Stability in storage | |
|---|---|---|---|---|---|---|---|---|---|---|---|
| | (A) component | (B) component | (C) component | (D) component | (E) component | (F) component | Other component | Soft-ness | Elastic-ity | 20° C. | 40° C. |
| Examples | | | | | | | | | | | |
| 2-13 | A-2 (15.0) | B-1 (1.5) | C-1 (1.5) | D-1 (2.5) | — | — | G-6(1.0) | '+2 | '+2 | o | o |
| 2-14 | A-3 (15.0) | — | C-3 (1.5) | D-1 (2.5) | — | F-1 (2.0) | G-2(1.0) | '+2 | '+2 | o | o |
| 2-15 | A-3 (15.0) | B-3 (1.0) | C-1 (1.0) | D-1 (2.0) | E-1 (1.0) | F-2 (2.0) | H-2(0.8) | '+2 | '+2 | o | o |
| 2-16 | A-3 (15.0) | — | C-1 (3.0) | D-2 (3.0) | E-2 (1.0) | F-3 (2.0) | G-7(1.0) H-6(0.6) | '+2 | '+2 | o | o |
| 2-17 | A-4 (15.0) | — | C-2 (4.0) | — | — | — | H-4(1.0) H-7(0.9) | '+2 | '+2 | o | o |
| 2-18 | A-4 (15.0) | B-2 (1.5) | — | D-1 (3.0) | — | — | G-8(1.0) | '+2 | '+2 | o | o |
| 2-19 | A-4 (15.0) | — | — | D-1 (2.5) | — | F-2 (2.0) | G-4(0.8) | '+2 | '+2 | o | o |
| 2-20 | A-5 (15.0) | B-4 (1.5) | C-3 (1.5) | D-1 (3.0) | E-5 (1.0) | — | H-2(1.5) H-8(0.8) | '+2 | '+2 | o | o |
| 2-21 | A-5 (15.0) | — | C-2 (2.0) | D-2 (3.0) | E-4 (1.0) | F-3 (2.0) | G-1(1.5) H-1(0.4) | '+2 | '+2 | o | o |
| 2-22 | A-6 (15.0) | — | C-1 (3.0) | — | — | F-1 (2.0) | G-10(1.0) | '+2 | '+2 | o | o |
| 2-23 | A-6 (15.0) | B-1 (1.5) | — | D-1 (3.0) | — | F-1 (2.0) | G-9(0.5) H-8(0.2) | '+2 | '+2 | o | o |

TABLE 2-10

| | Composition for soft-finishing agent | | | | | | | | | Stability in storage | |
|---|---|---|---|---|---|---|---|---|---|---|---|
| | (A) component | (B) component | (C) component | (D) component | (E) component | (F) component | Other component | Soft-ness | Elastic-ity | 20° C. | 40° C. |
| Comparative Examples | | | | | | | | | | | |
| 2-1 | — | — | C-1 (1.5) | — | — | F-1 (2.0) | Distearyl dimethylammonium chloride(15) | '0 | '−1 | o | Gel formed |
| 2-2 | — | — | — | D-1 (2.5) | E-1 (1.0) | — | Distearyl dimethylammonium chloride(15) | '0 | '−1 | Gel formed | Gel formed |
| 2-3 | — | B-1 (1.5) | C-1 (1.0) | D-1 (2.5) | — | F-1 (2.0) | Distearyl dimethylammonium chloride(15) | '+1 | '−1 | o | Separation |
| 2-4 | — | B-1 (1.5) | C-1 (2.0) | D-1 (3.0) | E-2 (1.0) | F-2 (2.0) | Distearyl dimethylammonium chloride(15) | '0 | '0 | o | Separation |
| 2-5 | — | — | — | D-2 (3.0) | — | — | Distearyl dimethylammonium chloride(15) | '+1 | '0 | Gel formed | Gel formed |
| 2-6 | — | — | C-3 (2.0) | D-2 (3.0) | — | F-2 (2.0) | Distearyl dimethylammonium chloride(15) | '0 | '0 | o | Separation |

The numerals enclosed by parenthesis in Tables 2-8 to 2-10 denote amounts of relevant components incorporated in relevant compositions, indicated in % by weight. The balances are accounted for by water.

It is evident from the results given above that the compositions of softener composition of the present invention were capable of imparting highly satisfactory softness and elasticity to fibers and were excellent in stability in storage.

What is claimed is:

1. A liquid softener or hair treating composition, comprising (A) a quaternary ammonium salt and water and having said (A) component present in said composition in an amount of 2 to 40% by weight, wherein said quaternary ammonium salt is of the general formula (1)

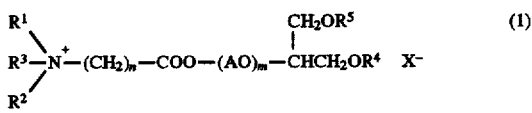

(wherein $R^1$, $R^2$, and $R^3$ are the same or different from each other and are alkyl groups or hydroxyalkyl groups 1 to 4 carbon atoms, $R^4$ and $R^5$ are the same or different from each other and are unsubstituted or hydroxyl group-substituted linear or branched alkyl group or alkenyl group of 8 to 36 carbon atoms, A is a linear or branched alkylene group of 2 or 3 carbon atoms, X is an anion group, n is an integer in the range of 1 to 6, and m is a numeral in the range of 0 to 20.

2. The composition according to claim 1, wherein said (A) component is represented by the general formula (I-1)

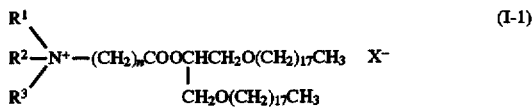

(wherein $R^1$, $R^2$, and $R^3$, n and $X^-$ have the same meanings as defined in claim 1.

3. The composition according to claim 1, wherein $R^1$, $R^2$, and $R^3$ are methyl group and $R^4$ and $R^5$ are a linear or branched alkyl group of 12 to 24 carbon atoms.

4. The composition according to claim 1, which further comprises the following components (B), (C), (D) and/or (E) and (F) in weight percentages based on the composition, (B): 0 to 20% of a linear or branched saturated or unsaturated alcohol of 8 to 44 carbon atoms, (C): 0 to 20% of a linear or branched saturated or unsaturated fatty acid of 8 to 36 carbon atoms, (D): 0–10% of a monohydric alcohol of 1 to 4 carbon atoms, (E): 0 to 10% of a polyether compound obtained by alkoxylation with ethylene oxide and optionally propylene oxide and/or trimethylene oxide of a compound having 3 or more active hydrogen atoms, said polyether compound having a weight average molecular weight in the range of 5,000 to 2,000,000, and having oxyethylene groups in an amount of not less than 55% by weight based on the molecular weight, or a derivative of said polyether compound, and (F): 0 to 10% of a nonionic surfactant of a linear or branched saturated or unsaturated alcohol of 8 to 24 carbon atoms alkoxylated with 5 to 50 mols of ethylene oxide, propylene oxide or mixture thereof.

5. A method for soft-finishing fibers, comprising treating fibers with a composition according to claim 1.

6. The method according to claim 5, wherein said fibers are cotton, acrylic or polyester fibers.

7. A method for treating hair, comprising treating hair with a composition according to claim 1.

8. A method for the production of a quaternary ammonium salt of the general formula (1)

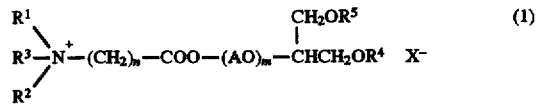

wherein $R^1$, $R^2$, and $R^3$ are the same or different from each other and are alkyl groups or hydroxyalkyl groups of 1 to 4 carbon atoms, $R^4$ and $R^5$ are the same or different from each other and are unsubstituted or hydroxyl group-substituted linear or branched alkyl group or alkenyl group of 8 to 36 carbon atoms, A is a linear or branched alkylene group of 2 or 3 carbon atoms, X is an anion group, n is an integer in the range of 1 to 6, and m is a numeral in the range of 0 to 20, comprising reacting a glycerol represented by the general formula (2)

(wherein $R^4$, $R^5$, A, and m have the same meanings as defined above), with a compound represented by the general formula (3)

wherein $R^6$ is a hydrogen atom or an alkyl group of 1 to 4 carbon atoms and Y is a halogen atom, and n has the same meaning as defined above) to esterify the compound of the formula (3) and producing a haloester represented by the general formula (4)

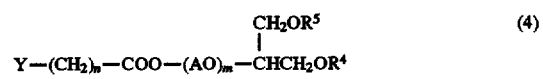

(wherein $R^4$, $R^5$, A, Y, n and m have the same meanings as defined above), and further reacting this haloester of the formula (4) with a tertiary amine represented by the general formula (5)

(wherein $R^1$, $R^2$, and $R^3$ have the same meanings as defined above).

9. A method for the production of a quaternary ammonium salt according to claim 8, comprising reacting a haloester represented by the general formula (4) as defined in claim 3 with a secondary amine represented by the general formula (6)

(wherein $R^1$ and $R^2$ have the same meanings as defined above) thereby forming an aminoester represented by the general formula (7)

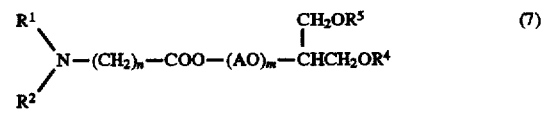

(wherein $R^1$, $R^2$, $R^4$, $R^5$, A, n, and m have the same meanings as defined above), and further reacting a quaternizing agent represented by the formula (8) with an aminoester of the formula (7)

(wherein $R^2$ and X have the same meanings as defined above).

10. A quaternary ammonium salt represented by the general formula (1)

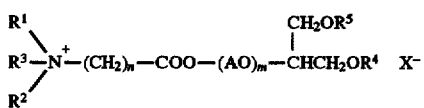

(1)

wherein $R^1$, $R^2$, and $R^3$ are the same or different from each other and are alkyl groups or hydroxyalkyl groups of 1 to 4 carbon atoms, $R^4$ and $R^5$ are the same or different from each other and are unsubstituted or hydroxyl group-substituted linear or branched alkyl group or alkenyl group of 8 to 36 carbon atoms, X is an anion group, and n is an integer in the range of 1 to 6.

11. A quaternary ammonium salt represented by the general formula (1)

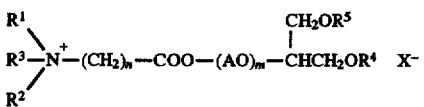

(1)

wherein $R^1$, $R^2$, and $R^3$ are the same or different from each other and are alkyl groups or hydroxyalkyl groups of 1 to 4 carbon atoms, $R^4$ and $R^5$ are the same or different from each other and are unsubstituted or hydroxyl group-substituted linear or branched alkyl group or alkenyl group of 8 to 36 carbon atoms, A is a linear or branched alkylene group of 2 or 3 carbon atoms, X is an anion group, n is 1 and m is a numeral in the range of 0 to 20.

12. A quaternary ammonium salt represented by the general formula (I-1)

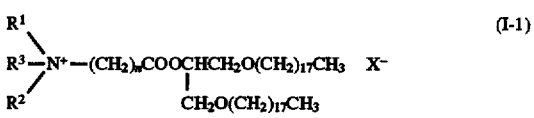

(I-1)

wherein $R^1$, $R^2$, and $R^3$ are the same or different from each other and are alkyl groups or hydroxyalkyl groups of 1 to 4 carbon atoms, n is an integer in the range of 1 to 6, and X is an anion group.

* * * * *